(12) United States Patent
Nawrocki

(10) Patent No.: US 9,494,651 B2
(45) Date of Patent: Nov. 15, 2016

(54) METHOD FOR TESTING EMBEDDED SYSTEMS

(71) Applicant: Andrzej Wlodzimierz Nawrocki, Port Coquitlam (CA)

(72) Inventor: Andrzej Wlodzimierz Nawrocki, Port Coquitlam (CA)

(73) Assignee: Honeywell Limited, Mississauga (CA)

( * ) Notice: Subject to any disclaimer, the term of this patent is extended or adjusted under 35 U.S.C. 154(b) by 190 days.

(21) Appl. No.: 14/592,585

(22) Filed: Jan. 8, 2015

(65) Prior Publication Data

US 2016/0202310 A1  Jul. 14, 2016

(51) Int. Cl.
| | |
|---|---|
| *G01R 31/28* | (2006.01) |
| *G01R 31/3187* | (2006.01) |
| *G01R 31/3185* | (2006.01) |
| *G01R 31/3167* | (2006.01) |
| *H02M 1/00* | (2006.01) |
| *G01N 1/00* | (2006.01) |

(52) U.S. Cl.
CPC ........ *G01R 31/3187* (2013.01); *G01R 31/3167* (2013.01); *G01R 31/318508* (2013.01); *G01N 1/00* (2013.01); *G01N 2201/00* (2013.01); *H02M 1/00* (2013.01)

(58) Field of Classification Search
CPC ...... G01N 1/00; G01N 2201/00; C12Q 1/00; C12Q 2304/00; G05F 1/00; H02M 1/00
See application file for complete search history.

(56) References Cited

U.S. PATENT DOCUMENTS

| | | | |
|---|---|---|---|
| 6,842,865 B2 | 1/2005 | Nee | |
| 7,188,276 B2 | 3/2007 | Yun | |
| 9,140,752 B2 * | 9/2015 | Oshima | G01R 31/3177 |
| 2005/0039079 A1 * | 2/2005 | Higashi | G01R 31/3183 714/28 |
| 2006/0250149 A1 | 11/2006 | Lan | |
| 2008/0020712 A1 * | 1/2008 | Meagher | G01R 31/2846 455/67.14 |
| 2014/0095931 A1 * | 4/2014 | Sadasivam | G06F 11/3664 714/28 |
| 2015/0145524 A1 * | 5/2015 | Duncan | G01R 31/024 324/538 |
| 2015/0234764 A1 * | 8/2015 | Kline | G06F 13/126 710/5 |
| 2015/0234765 A1 * | 8/2015 | Kline | G06F 13/4022 710/316 |

\* cited by examiner

*Primary Examiner* — Jermele M Hollington
*Assistant Examiner* — Temilade Rhodes-Vivour
(74) *Attorney, Agent, or Firm* — Charles H Jew

(57) ABSTRACT

Functional diagnostic testing of an electronic circuit board assembly with one or more embedded channels to be tested includes steps of: (a) connecting a channel under test; (b) imposing a known digital or analog voltage, as appropriate for a channel under test, that is generated by a digital or analog output of the electronic circuit board assembly; and (c) comparing data read by the channel under test with the stored value of the imposed voltage and required tolerance to determine whether the channel under test is within specifications. Diagnostic test implemented by digital logic and software residing onboard the electronic circuit board assembly. Execution of software or firmware code segment controls the diagnostic test sequence. Signal switching is facilitated by digital and analog multiplexers.

16 Claims, 3 Drawing Sheets

METHOD FOR TESTING EMBEDDED SYSTEMS

FIELD OF THE INVENTION

The invention relates to testing of complex electronic circuit board assemblies. In particular, the invention relates to techniques for functional testing of embedded systems that contain System on Chip (SoC), Programmable System on Chip (PSoC), System in Package (SiP) or other integrated circuits (IC).

BACKGROUND OF THE INVENTION

SoC devices typically include the following components on a single substrate:

(1) microcontroller, microprocessor or digital signal processor (DSP) core(s); and some SoCs that are referred to as multiprocessor systems on chip (MPSoC), may include more than one processor core;

(2) memory blocks including ROM, RAM, EEPROM and Flash memory;

(3) timing sources including oscillators and phased-locked loops;

(4) peripherals including counter, timers and real-time timers, (5) external interfaces including USB, FireWire, Ethernet, USART, SPI, I2C, (6) analog interfaces including ADCs and DACs;

(7) voltage regulators and power management circuits; and (8) various user configurable general-purpose input and output (GPIO) pins.

The manufacture of electronic circuit board assemblies consists of two basic stages: board assembly and board testing. Testing may involve an in-circuit test and/or a functional test. In-circuit testing verifies that the board has been assembled according to vendor manufacturing specifications. Functional testing ensures that acceptable electronic circuits perform functions as designed. Testing of sophisticated electronic circuits requires a complex test system that may entail extensive functional testing protocols and expensive and intricate test fixtures. The process is labor intensive unless it is fully automated.

Implementing suitable test fixtures can be technically challenging and expensive; moreover, the test fixture is often designed only after the circuit board has been completed and prototypes built and tested. This approach causes unnecessary delays in production and product release.

For a simple electronic test system, one or more test signals are applied to a device under test (DUT) and the response of the unit is measured at one or more locations and compared with the responses that would be attained by a standard, operating circuit. Exemplary testing techniques include: (1) "Flying Probe" testing; (2) ROM (Read Only Memory) emulation, (3) using a debug port for testing; (4) using a complex test fixture connecting to each test point on a DUT; and (5) using a complex test system emulating behavior of each external device, which is normally connected to a DUT in an operation mode. These methods are generally difficult to implement in manufacturing processes.

An example of a test fixture for testing a complex circuit board is described in U.S. Patent No. 2006/0250149 to Lan and features a testing platform, a base disposed on the testing platform, a probe coupled to the testing platform and disposed on the base, and a conversion board disposed between the bases. The test fixture's main disadvantage is its mechanical complexity that requires a chain of multiple connections between a test point on the DUT and a probe. Lan does not address functional testing of circuit boards.

Another example of a test system for testing electronic boards that contain at least one processor is described in U.S. Pat. No. 6,842,865 to Nee et al. The test system includes a processor control unit that is connected to a DUT and which runs test routines on the DUT. The system also contains an electronic circuit emulating at least one peripheral device, which is connected to the DUT, a response circuit measuring a response of the DUT to a test routine and a main controller, which communicates with the response circuit in order to obtain the results of the test routine. The complex test system requires much external hardware and complex software to implement.

Finally, an illustrative apparatus for testing computer systems using a complex test fixture is described in U.S. Pat. No. 7,188,276 to Yun. The test fixture incorporates a controller, which controls the testing of the computer system, a field programmable gate array (FPGA) and several programmable memory modules. Each programmable memory module stores configuration data of peripheral devices of the computer system in corresponding versions respectively. Its complexity is the system's major drawback in that it requires external hardware to emulate external components and requires maintaining various versions of programmable memory modules to accommodate different versions of systems being tested.

SUMMARY OF THE INVENTION

This present invention takes advantage of several features that almost any electronic board assembly including SoC already utilizes during normal operations. The invention eliminates shortcomings of prior art test systems and provides a simple and cost-effective method of testing embedded electronic circuits in the manufacturing environment and, in addition, provides on-line diagnostic capability in the industrial environment.

In one aspect, the invention is directed to a system for testing complex electronic circuit board assemblies containing sufficient digital logic processing and input and output means to perform diagnostic self-tests on the functional characteristics of the complex electronic circuit board assemblies that includes:

(a) a complex electronic circuit board containing at least one integrated circuit that can provide data processing, data storage, external data communications, and digital and analog input/output functions such as a System on Chip (SoC) device, a Programmable System on Chip (PSoC), a System in Package (SiP), or other similar devices;

(b) software or firmware code segment providing the instructions for the diagnostic self-tests residing in the at least one integrated circuit as part of the primary code controlling the primary functions of the complex electronic circuit board assembly;

(c) a display to indicate the pass/fail results of the diagnostic self-tests, such as, for example, color LEDs or a LCD;

(d) at least one digital multiplexer controlled by the at least one integrated circuit to switch the source of the input signals between internal simulated digital test signals generated by the at least one integrated circuit and externally generated measurement and control digital input/output signals;

(e) at least one analog multiplexer controlled by the at least one integrated circuit to switch the source of the input signals between internal simulated analog test signals generated by the at least one integrated circuit and externally generated measurement and control analog input/output signals; and (f) software or firmware code segment that controls the switching between internally generated simulated test signals during diagnostic self-test and externally generated measurement and control signals, and that compares the measured simulated test signals with stored acceptable values of the measured simulated test signals to determine whether the channel of the complex electronic circuit board being tested is within functional specifications.

In another aspect, the invention is directed to a method for functional diagnostic testing of complex electronic circuit board assemblies, which have one or more channels to be tested, wherein the diagnostic tests are conducted by digital logic and software residing onboard a complex electronic circuit board assembly that imposes a known digital or analog voltage or current, as appropriate for the channel under test, that is generated by a digital or analog output of the complex electronic circuit board assembly and electrically connected to the channel under test by either a wiring harness or by a digital or analog multiplexer, and the data read by the channel under test is compared with the stored value of the imposed voltage and required tolerance to determine whether the channel under test is within specifications. The method includes the steps of:

(a) electrically connecting a channel under test for example by connecting the wiring harness, if one is required, to appropriate connectors on the complex electronic circuit board assembly;

(b) applying an instruction to the complex electronic circuit board assembly to initiate execution of a software or firmware code segment that controls the diagnostic test, for example, by closure of a hardware switch built onto the complex electronic circuit board that is connected to at least one integrated circuit or by sending a software command to the complex electronic circuit board via an external communication means;

(c) the software or firmware code segment sequentially connects predetermined output analog channels to predetermined analog input channels, applies a predetermined voltage or current and measures the value from the connected analog input channel;

(d) the software or firmware code segment compares a value read from the connected analog input channel to the applied predetermined voltage or current and calculates whether the value measured is within a specified tolerance for that channel;

(e) the software or firmware code segment outputs a signal to an indicator LED, LCD, or to the external communications means to indicate the functional status, or optionally the voltages or currents measured, of the channels under test;

(f) the software or firmware code segment sequentially connects predetermined output digital channels to predetermined digital input channels, applies a predetermined value and measures a value from the connected digital input channel;

(g) the software or firmware code segment compares a value read from the connected digital input channel to the applied value and calculates whether the channels are functional; and (h) the software or firmware code segment outputs a signal to an indicator LED, LCD, or to the external communications means to indicate the functional status, or optionally the voltages or currents measured, of the channels under test.

DETAILED DESCRIPTION OF THE PREFERRED EMBODIMENTS

A typical SoC circuit interfaces with a number of field devices either through analog or digital inputs and outputs. Typically, an analog input signal is a voltage from a sensor or transducer, which represents a measurement of various physical parameters: temperature, pressure, moisture etc. An analog output signal (voltage) represents a control signal, which is sent to a transducer or actuator to adjust various physical parameters. A digital output signal (single bit) typically represents a control signal that is used to change the status of a field device, e.g. turn a bulb on. A digital input signal is used to monitor a status of the field device, e.g., heater is off.

Figure 1:
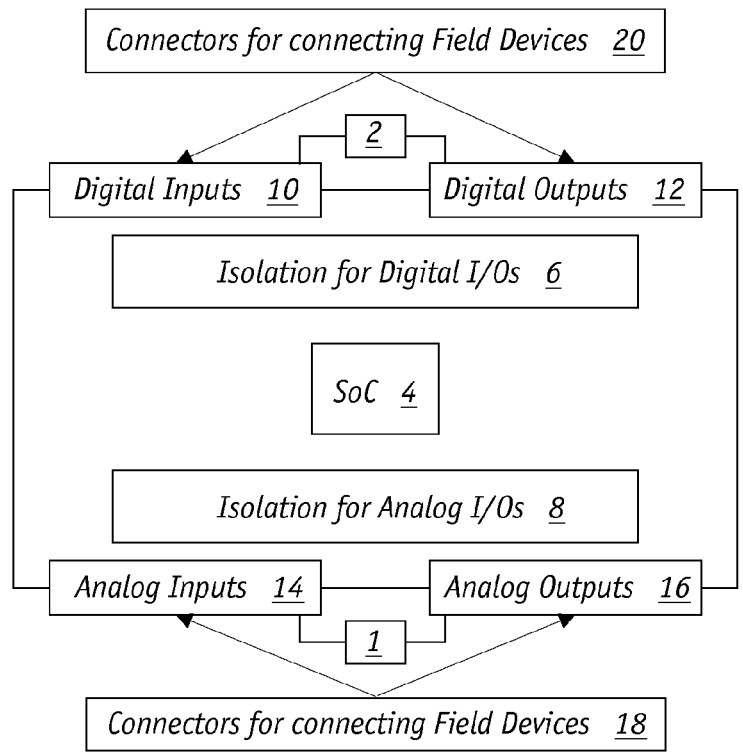
FIG. 1 illustrates a SoC-based board assembly.

A typical design using SoC includes an electronic circuitry that isolates (separates) low voltage portion of the circuit (SoC and associated digital and analog circuits directly connected to SoC) from that part of the circuit that directly interfaces with field devices. This separation is used to isolate external devices, which typically require much higher voltages to operate (e.g. powered from +12VDC, +15VDC, +24VDC etc.). FIG. 1 shows a simplified block diagram of a SoC-based electronic board assembly 2 which includes a SoC 4, isolation for digital inputs/outputs 6, digital inputs 10, digital outputs 12, connectors for connecting field devices 20, isolation for analog inputs/outputs 8, analog inputs 14, analog outputs 16 and connectors for connecting field devices 18. Wire harness 2 connects digital inputs with digital outputs and wire harness 1 connects analog inputs with analog outputs.

Figure 2:
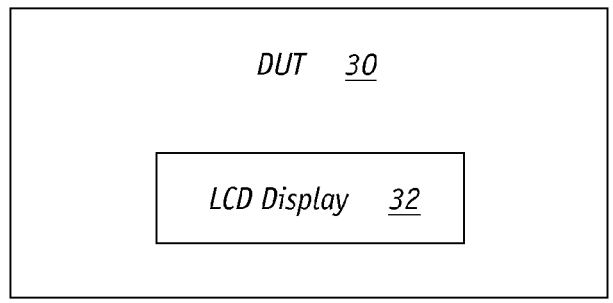
FIG. 2 illustrates a DUT that includes an LCD display.

When a LCD display 32 is also included in the design of an electronic board, a test system can consist of only of a DUT 30 as shown in FIG. 2. (The DUT 30 can be similar to DUT depicted in FIG. 1.) In this configuration, behavior and status of all field devices are simulated by the test program. In some cases where field devices need to be simulated externally, a simple test fixture may need to be built for this purpose. In one embodiment, the test fixture could include just a set of loop-back cables connecting digital inputs with digital outputs and analog inputs with analog outputs. If inputs and outputs require different voltages some additional circuitry may need to be used to adjust voltage levels to desired values. These additional circuits could be either implemented as part of a DUT or on the test fixture.

Figure 3:
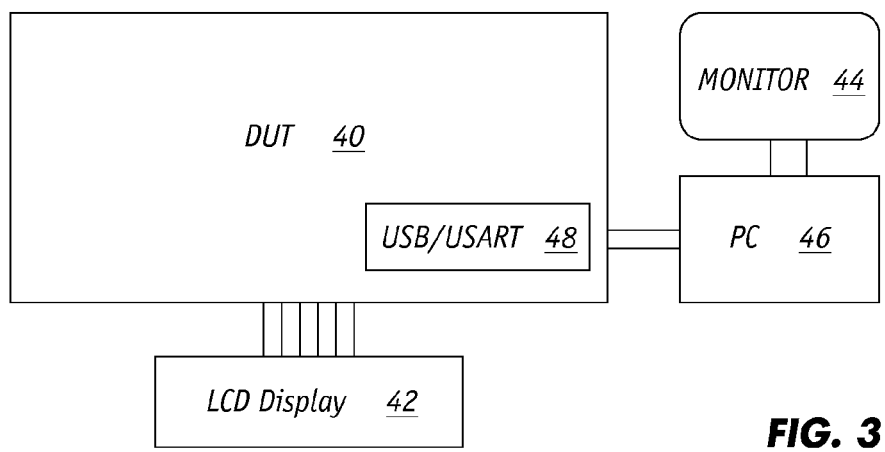
FIG. 3 illustrates a DUT that does not include an LCD display.

When LCD display is not a part of DUT, an external LCD 42 may be connected to a DUT 40 through a dedicated connector as shown in FIG. 3. Since a typical SoC has already built-in interfaces for USB, Ethernet, USART etc. 48, test results can also be sent to an external PC 46 or a web server and displayed on an external monitor 40.

A preferred method of implementing the invention is to include a test program within the main program of SoC (e.g., as a subroutine). Typically this test program is a small portion of a code that is included in the main program. During normal operating mode only the main program is executed. The test program is executed only if a request to perform a test is received by the SoC. During normal operations, the SoC periodically checks if the request for the test has been received.

Figure 4:
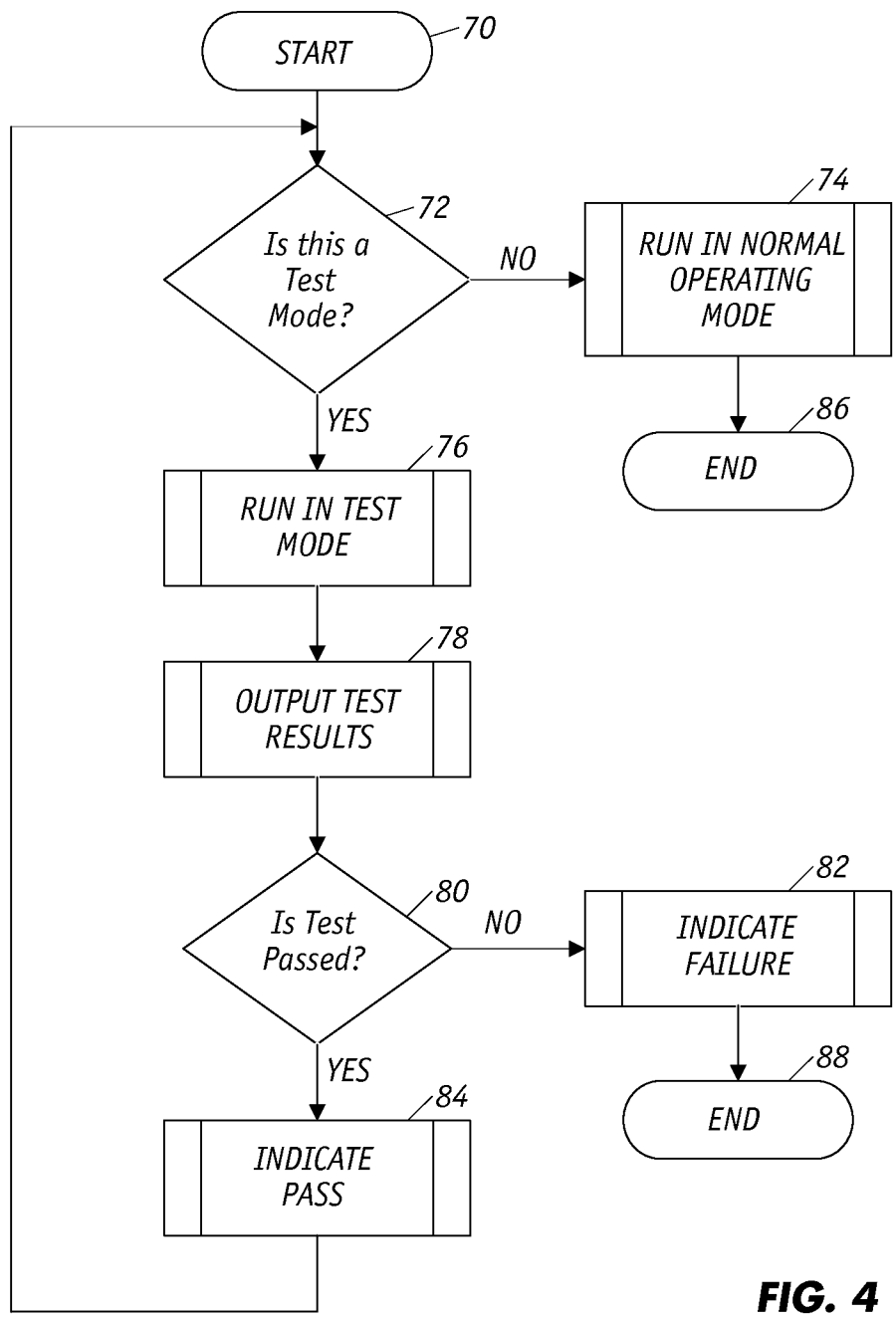
FIG. 4 is a flowchart of a test routine.

An example of a test sequence as shown in FIG. 4 begins with start step 70 and terminates at step 86 or 88 when the channel is determined to be operating normally 74 or if the channel fails the test 82. Specifically, a request for the execution of the test program can be initiated either through a hardware trigger, e.g. changing position of a jumper or toggling a switch mounted on DUT, or a software trigger (e.g., an interrupt) designated as step 72 ("Is this a Test Mode?"). After the request for executing the test program is detected, an appropriate portion of the code is executed to perform the required test routines 76. Results of the test can be displayed 78 on LCD display or sent to an external PC or server for displaying on an external monitor. If the channel fails the test at step 80, the results can be displayed 82 before the test routine is terminated. If the channel passes, the results can be displayed 84 before initiating inquiry step 72.

There are several options for displaying the test results. For example, a DUT can provide a simple and instantaneous display of the status of the test results using LEDs that are installed on the electronic board, where GREEN LED means "all test passed" and RED LED means "at least one of the test has failed". This method enables a very quick, fully automated, and efficient way of identifying boards that failed the test. Alternatively, an LCD display or PC monitor can be employed to provide identification of the failed tests (such as the specific channel that failed), the expected result (when operating normally) and the actual result (failure signature) in various forms (e.g., simple text message or graphical representation).

A test routine may include the following sub-routines: (1) Test Mode Routine, (2) Display Test Results Routine, (3) Display Test Passed Routine, and (4) Display Test Failed Routine Test Mode Routine In this routine, an algorithm continuously scans all analog and digital I/O values currently present at all GPIOs. All analog values representing measurement and control signals for analog devices (sensors, transducers, etc.) are stored in a single array, which holds all values in a predetermined order. An alternative is to store these values in several arrays, which may hold control signals and measured values separately for ease of indexing and further processing. Storing digital values does not require arrays. Since these values are typically single bits, they can be stored as a byte or a word (8-bit, 16-bit, 32-bit, etc.) or any combinations of these depending on the system scale (number of GPIOs required) and SoC architecture.

The expected values for both analog and digital signals are stored in separate memory locations. This could be separate arrays, hard-coded vales in a code or look-up tables.

During the Test Mode routine, scanned values are constantly compared with expected values and results of that operation are stored in a single array or several arrays depending on system complexity and number of GPIOs used. If results of all comparisons are positive, Test Flag variable is set to HIGH (where HIGH means "Test has passed"), if at least one comparison yields negative result, Test Flag is set to LOW (where LOW means "Test has failed").

Testing of digital inputs and outputs will require looping back digital inputs with digital outputs. That could be achieved either by using a combination of multiplexers and/or digital switches controlled by the test software or external hardware (e.g., wire harnesses).

Figure 5:
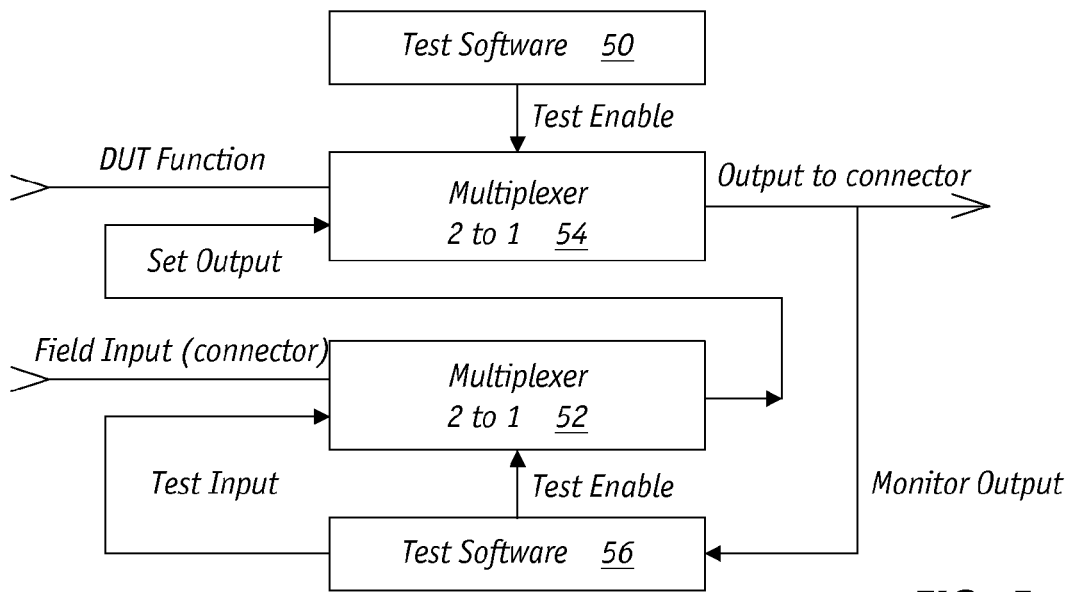
FIGS. 5 and 6 illustrate implementation of testing digital inputs and outputs, respectively.

FIG. 5 shows an implementation of testing a single digital input using two multiplexers 52,54 and a control algorithm in the form of test software 50,56. Multiplexer 52 has 2 inputs with one of its inputs being preferably hardwired to an input connector (used by field device to bring input signal). The second input is controlled by the test routine. The "TEST ENABLE" control signal from test software 56 determines a mode of operation of multiplexer 52; in normal mode, the field device input is selected and in the test mode the field device input is simulated by software. The output from the multiplexer 52 is connected to a second multiplexer (multiplexer 54) as a second input. The first input of the multiplexer 54 is generated on a board and is derived from the intended board functionality. The output of multiplexer 54 is connected directly to the output connector. The signal that appears on this output is controlled by the same "TEST ENABLE" signal. The output signal of the multiplexer 54 is monitored by the test program and is used for comparing input and output values that are stored in the data arrays.

Figure 6:
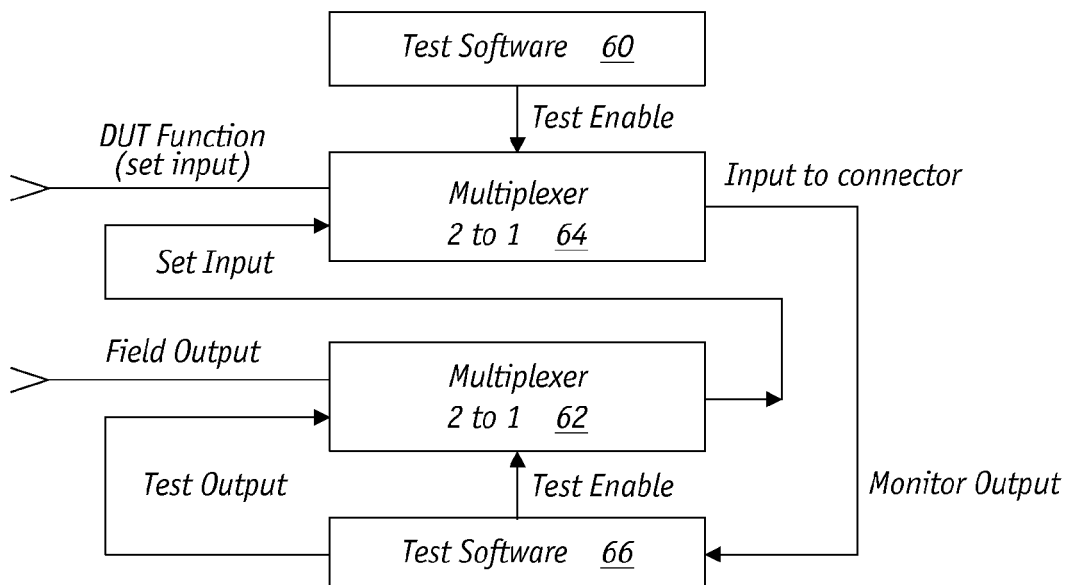

FIG. 6 shows an implementation of testing a single digital output using two multiplexers 60,62 and a control algorithm in the form of test software 60,66. This testing process is similar to that for testing a single digital input as shown in FIG. 5. Multiplex 62 receives a signal either from a field device or one that is simulated by test software 66. The output signal of multiplexer 62 is used to simulate output in the test mode. During normal operation multiplexer 64 will pass a signal that is derived from the intended board functionality to control digital output.

Testing of digital inputs is done by setting them either HIGH or LOW and verifying that corresponding outputs respond accordingly. Testing of digital outputs is very similar. In general, a routine for testing of digital inputs and outputs can use the same software architecture or hardware (e.g., wire harness).

Testing of analog inputs, in its simplest form, may only require a single value. In this case, a constant voltage is applied to each analog input and it is compared with an expected value stored in the data array. Similarly, testing of analog output will require measuring voltage at the output and comparing that value with one stored in the data array.

Testing of analog inputs and outputs can utilize a similar approach to that for testing digital inputs and outputs as illustrated in FIGS. 5 and 6. System generated input/output analog test signals can be compared with corresponding measured analog signals. If using a single analog value does not satisfy test requirements, a range of simulated analog values can be used. Furthermore, each analog input can use different voltages, different ranges of values or a combination of all above, depending on desired functionality. The test software may include a number of loops and various algorithms for testing different voltage ranges.

Display Test Results Routine

In this routine, algorithm continuously displays results of measured analog and digital values on LCD display. Typical information displayed may include a date and time of the test, a name of each monitored GPIO, a name of a parameter measured, parameter current value, parameter expected value and its engineering unit of measure (e.g. voltage, temperature, pressure, etc.).

Display Test Passed Routine

In this routine, algorithm displays "PASS" message on LCD display. Typical information displayed may also include a date and time of the test. In addition, the same message can be sent to an external PC and displayed on an external monitor. In addition a dedicated GREEN LED on the board is illuminated to provide a visible status that all tests have passed.

Individual test results for each parameter can be reviewed in this mode. By pushing dedicated buttons on the DUT, the test results can be viewed repeatedly in a predetermined order or selected randomly. In this mode corresponding values are being fetched from an array (arrays), which holds the measurement results. These results then gets converted to a desired format and displayed with its name and a unit of measure. Results for digital I/Os are displayed with its signal name and current status (typically either "ON" or "OFF"). The GREEN LED, displaying test status result, is set by the Test Flag variable.

Display Test Failed Routine

In this routine, algorithm displays a "FAILED" message on a LCD display. Typical information displayed may also include a date and time of test. In addition, the same message can be sent to an external PC and displayed on an external monitor. In addition a dedicated RED LED on the board is illuminated to provide a visible status that at least one test failed.

Individual test results for each parameter that has failed can be reviewed in this mode. By pushing dedicated buttons on the DUT the test results can be viewed repeatedly in a predetermined order or selected randomly. In this mode, values of parameters, which were flagged as failed, are being fetched from an array (arrays), which stores the measurement results and then converts these results to a desired format and displays them with its name and a unit of measure. Results for digital I/Os are displayed with its signal name and current status (typically either "ON" or "OFF"). The RED LED, displaying test status result, is set by the Test Flag variable.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A system for testing an electronic circuit board assembly containing digital logic processing and input and output means that perform diagnostic self-tests on functional characteristics of the electronic circuit board assembly that comprises:

an electronic circuit board containing an integrated circuit configured to provide data processing, data storage, external data communications, and digital input and output functions and analog input and output functions;

a first software or firmware code segment configured to provide instructions for diagnostic self-tests residing in the integrated circuit as part of a primary code controlling primary functions of the electronic circuit board assembly;

a display to indicate the pass/fail results of the diagnostic self-tests;

a digital multiplexer that is controlled by the integrated circuit to switch a source of input signals between internally generated digital test signals and externally generated measurement and control digital input/ output signals;

an analog multiplexer that is controlled by the integrated circuit to switch the source of the input signals between internal simulated analog test signals generated by the integrated circuit and externally generated measurement and control analog input and output signals; and a second software or firmware code segment configured to control the switching between internally generated simulated test signals during a diagnostic self-test and externally generated measurement and control signals, and that compares the measured simulated test signals with stored acceptable values of the measured simulated test signals to determine whether a channel of the electronic circuit board being tested is within functional specifications.

2. The system of claim 1 comprising an external communication means for transmitting diagnostic self-test results to a computer for data storage and for accepting commands from a computer to execute the diagnostic self-test or portions of the diagnostic self-test.

3. The system of claim 1 wherein the digital multiplexer and the analog multiplexer are augmented with a physical wiring harness that provides electrical connection between one or more electronic circuit board assembly outputs back to one or more electronic circuit board assembly inputs for testing.

4. The system of claim 1 wherein the integrated circuit comprises one or more devices that is selected from the group consisting of such as a system on chip (SoC) device, a programmable system on chip (PSoC), a system in package (SiP), and combinations thereof.

5. The system of claim 1 wherein the display comprises a color LED or LCD.

6. A method for functional diagnostic testing of a device under test that includes an electronic circuit board assembly that has one or more channels to be tested that comprises the steps of:

(a) electrically connecting a channel to be tested that is in the electronic circuit board assembly;

(b) imposing a known digital or analog voltage, as appropriate for a channel under test, that is generated by a digital or analog output of the electronic circuit board assembly; and (c) comparing data read by the channel that is electrically connected with a stored value of the imposed voltage and required tolerance to determine whether the channel that is electrically connected is within specifications, wherein diagnostic test of steps (b) and (c) is conducted by digital logic and software residing onboard the electronic circuit board assembly of the device under test.

7. The method of claim 6 wherein step (a) comprising using a wiring harness or using a digital or analog multiplexer circuit.

8. A method for functional diagnostic testing of an electronic circuit board assembly, which has one or more channels to be tested, wherein the diagnostic tests are conducted by digital logic and software residing onboard the electronic circuit board assembly that imposes a known digital or analog voltage or current, as appropriate for the channel under test, that is generated by a digital or analog output of the electronic circuit board assembly and electrically connected to the channel under test and the data read by the channel under test is compared with the stored value of the imposed voltage and required tolerance to determine whether the channel under test is within specifications, said method comprising the steps of:

(a) electrically connecting a channel under test to appropriate connectors on the electronic circuit board assembly;

(b) applying an instruction to the electronic circuit board assembly to initiate execution of a software or firmware code segment that controls the diagnostic test;

(c) sequentially connecting predetermined output analog channels to predetermined analog input channels, applying a predetermined voltage or current and measuring a value from the connected analog input channel;

(d) comparing a value read from the connected analog input channel to the applied predetermined voltage or current and calculating whether the value measured is within a specified tolerance for that channel;

(e) outputting a signal to indicate the functional status or the voltages or currents measured, of the channels under test;

(f) sequentially connecting predetermined output digital channels to predetermined digital input channels, applying a predetermined value and measuring a value from the connected digital input channel;

(g) comparing a value read from the connected digital input channel to the applied value and calculating whether the channels are functional; and (h) outputting a signal to indicate the functional status, or optionally the voltages or currents measured, of the channels under test.

9. The method of claim 8 wherein step (a) comprises connecting a wiring harness to the connectors.

10. The method of claim 8 wherein step (a) employs at least one of a digital multiplexer or analog multiplexer.

11. The method of claim 8 wherein step (b) comprises closing a hardware switch built onto the electronic circuit board that is connected to an integrated circuit.

12. The method of claim 8 wherein step (b) comprises sending a software command to the electronic circuit board via an external communications device.

13. The method of claim 8 wherein step (e) comprises outputting a signal to an indicator LED or LCD.

14. The method of claim 8 wherein step (e) comprises outputting a signal to an external communications device.

15. The method of claim 8 wherein step (h) comprises outputting a signal to an indicator LED or LCD.

16. The method of claim 8 wherein step (h) comprises outputting a signal to an external communications device.

* * * * *